United States Patent
Wildeman et al.

(10) Patent No.: US 9,187,851 B2
(45) Date of Patent: Nov. 17, 2015

(54) STITCH BONDED CREPED FABRIC CONSTRUCTION

(75) Inventors: Martin Wildeman, Spartanburg, SC (US); Lori Shannon Sears, Taylors, SC (US)

(73) Assignee: Tietex International Ltd., Spartanburg, SC (US)

(*) Notice: Subject to any disclaimer, the term of this patent is extended or adjusted under 35 U.S.C. 154(b) by 561 days.

(21) Appl. No.: 13/523,410

(22) Filed: Jun. 14, 2012

(65) Prior Publication Data

US 2012/0323197 A1  Dec. 20, 2012

Related U.S. Application Data

(60) Provisional application No. 61/497,260, filed on Jun. 15, 2011.

(51) Int. Cl.

| | |
|---|---|
| *D04H 1/52* | (2006.01) |
| *D04B 23/10* | (2006.01) |
| *D04B 21/14* | (2006.01) |
| *D04H 1/4291* | (2012.01) |
| *D04H 1/435* | (2012.01) |
| *D04H 3/007* | (2012.01) |
| *D04H 3/011* | (2012.01) |
| *D04H 3/115* | (2012.01) |
| *D04H 3/16* | (2006.01) |
| *A61F 13/537* | (2006.01) |
| *A61F 13/53* | (2006.01) |

(52) U.S. Cl.
CPC ............ *D04H 1/52* (2013.01); *A61F 13/53713* (2013.01); *A61F 13/53717* (2013.01); *A61F 13/53747* (2013.01); *D04B 21/14* (2013.01); *D04B 23/10* (2013.01); *D04H 1/4291* (2013.01); *D04H 1/435* (2013.01); *D04H 3/007* (2013.01); *D04H 3/011* (2013.01); *D04H 3/115* (2013.01); *D04H 3/16* (2013.01); *A61F 2013/530671* (2013.01); *A61F 2013/53786* (2013.01); *Y10T 428/24273* (2015.01); *Y10T 428/24446* (2015.01)

(58) Field of Classification Search
CPC .......... D04B 23/10; D04B 2/08; D04B 21/14; D04B 21/1453
See application file for complete search history.

(56) References Cited

U.S. PATENT DOCUMENTS

| | | | | |
|---|---|---|---|---|
| 4,773,238 A | * | 9/1988 | Zafiroglu | 66/192 |
| 4,876,128 A | * | 10/1989 | Zafiroglu | 428/102 |
| 4,891,957 A | * | 1/1990 | Strack et al. | 66/192 |
| 4,998,421 A | * | 3/1991 | Zafiroglu | 66/192 |
| 5,187,952 A | * | 2/1993 | Zafiroglu | 66/192 |

(Continued)

OTHER PUBLICATIONS

International Search Report and Written Opinion of the International Searching Authority in PCT/US2012/042492 dated Feb. 1, 2013 issued by ISA/KR.

*Primary Examiner* — Danny Worrell
(74) *Attorney, Agent, or Firm* — J.M. Robertson, LLC

(57) ABSTRACT

A stitch-bonded fabric construction in which broadly spaced parallel linear stitch lines are applied through a very low weight fibrous substrate to stabilize the substrate in the machine direction. Texture is imparted by applying significant overfeed conditions to the stitching substrate thereby causing a substantial bunching of the substrate at the stitching position. The resulting product has an arrangement of alternating ridges and valleys running predominantly in the cross-machine direction. The stabilizing linear stitch lines lock in the puckered texture.

13 Claims, 3 Drawing Sheets

(56) References Cited

U.S. PATENT DOCUMENTS

| | | | |
|---|---|---|---|
| 5,192,600 A * | 3/1993 | Pontrelli et al. | 428/102 |
| 5,247,893 A * | 9/1993 | Zafiroglu | 112/475.08 |
| 5,474,006 A * | 12/1995 | Anzilotti et al. | 112/410 |
| 5,623,888 A * | 4/1997 | Zafiroglu | 112/414 |
| 5,679,438 A * | 10/1997 | Ramdin et al. | 428/152 |
| 5,692,777 A * | 12/1997 | Tochacek et al. | 280/743.1 |
| 6,124,001 A | 9/2000 | Sugita et al. | |
| 6,407,018 B1 * | 6/2002 | Zafiroglu | 442/336 |
| 6,787,212 B2 * | 9/2004 | Strength et al. | 428/102 |
| 6,855,220 B2 * | 2/2005 | Wildeman | 156/66 |
| 6,855,392 B2 * | 2/2005 | Wildeman et al. | 428/88 |
| 6,951,590 B2 * | 10/2005 | Zafiroglu et al. | 156/72 |
| 6,967,052 B2 * | 11/2005 | Zafiroglu | 428/102 |
| 7,775,170 B2 * | 8/2010 | Zafiroglu | 112/475.08 |
| 7,875,334 B2 * | 1/2011 | Zafiroglu et al. | 428/105 |
| 8,021,735 B2 * | 9/2011 | Tsiarkezos | 428/88 |
| 8,685,521 B2 * | 4/2014 | Yanagawase et al. | 428/102 |
| 8,690,850 B2 * | 4/2014 | Hardegree | 604/385.24 |
| 8,809,213 B2 * | 8/2014 | Wildeman et al. | 442/351 |
| 8,834,984 B2 * | 9/2014 | Wildeman | 428/107 |
| 2003/0207637 A1 | 11/2003 | Wildeman | |
| 2008/0166520 A1 | 7/2008 | Zafiroglu | |
| 2008/0280094 A1 * | 11/2008 | Wildeman et al. | 428/91 |
| 2010/0263152 A1 * | 10/2010 | Wildeman | 15/228 |
| 2010/0263154 A1 * | 10/2010 | Wildeman et al. | 15/244.4 |
| 2011/0028936 A1 * | 2/2011 | Wildeman et al. | 604/391 |
| 2012/0323197 A1 * | 12/2012 | Wildeman et al. | 604/367 |

* cited by examiner

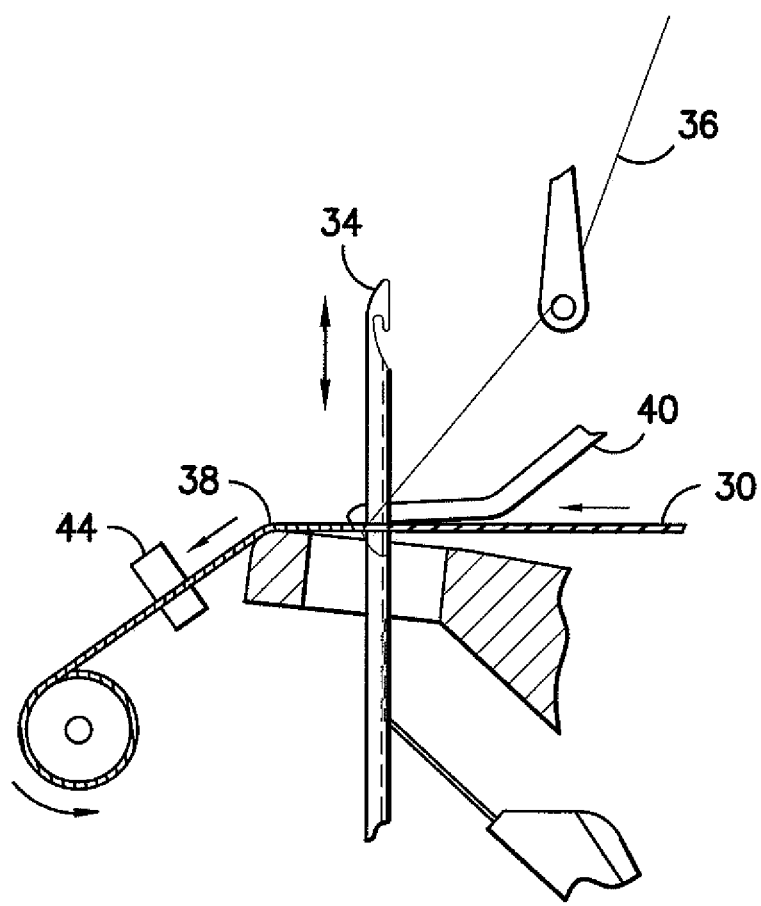
FIG. -1-

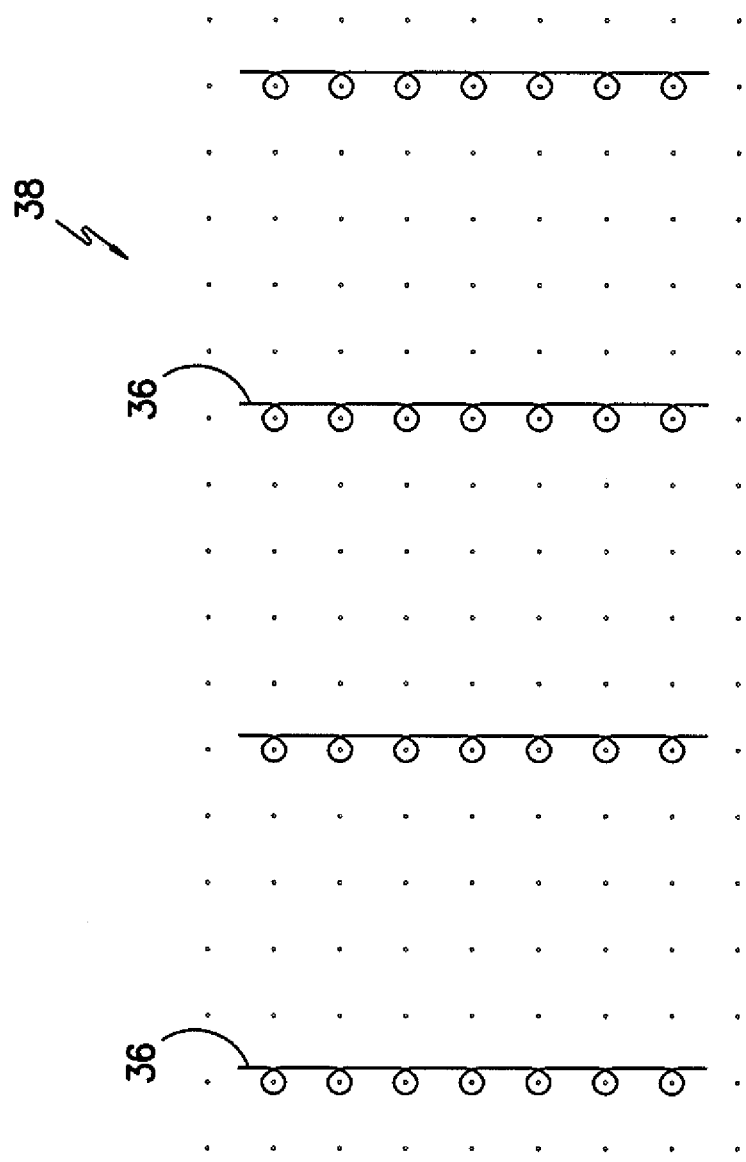
FIG. -2-

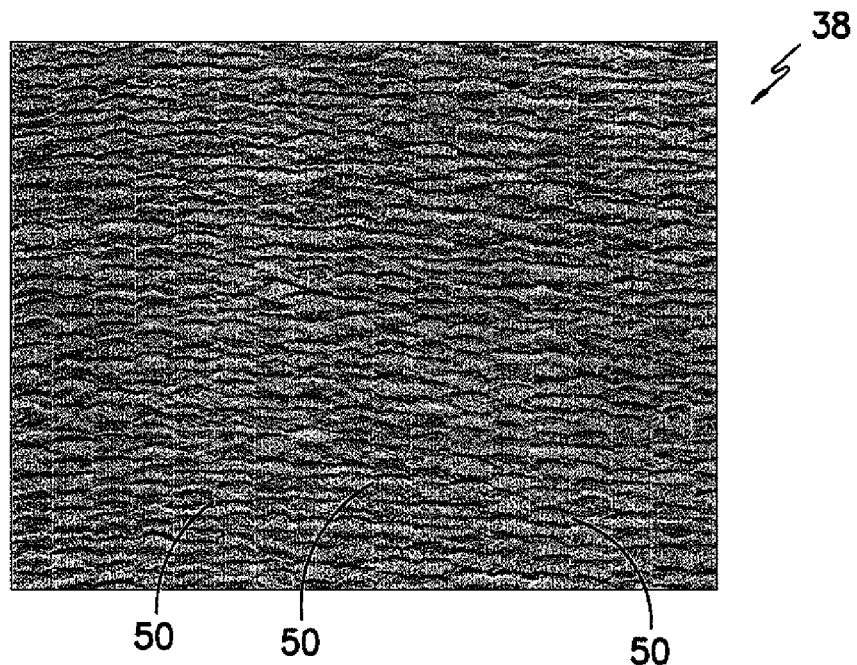
FIG. -3-
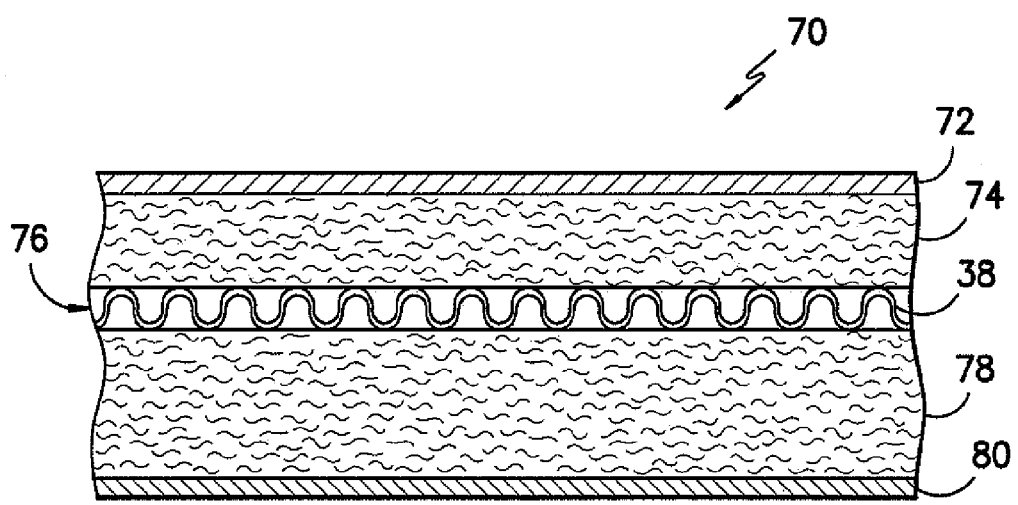
FIG. -4-

STITCH BONDED CREPED FABRIC CONSTRUCTION

CROSS-REFERENCE TO RELATED APPLICATION

This filing claims the benefit of, and priority from U.S. provisional application 61/497,260 filed Jun. 15, 2011, the contents of which are incorporated by reference herein in their entirety.

TECHNICAL FIELD

The present disclosure relates generally to a fabric construction, and more particularly, to a fabric construction adapted for use in applications such as a cleaning wipe or fluid acquisition layer in a diaper. The fabric construction is formed by stitch-bonding and has a contoured creped surface. A method for forming such materials is also provided.

BACKGROUND OF THE DISCLOSURE

Hand wipe products have recently gained popularity as a mechanism for cleaning and disinfecting surfaces. Such wipe products typically incorporate a nonwoven sheet which is saturated with a cleaning and sanitizing solution. By way of example only, such wipe products are available at many grocery stores for use by customers to clean the surfaces of grocery carts and baskets before use. Such wipe products are also sold for home use.

In existing wipe products the sheet material acts primarily as a carrier for the cleaning or disinfecting solution and must have sufficient thickness to avoid tearing during use. Flat or textured non-woven sheets have been used successfully, but such nonwoven sheets must have a relatively substantial weight to avoid falling apart during use. Thus, relatively substantial quantities of fiber are required to form such sheets. The use of additional fiber has the undesired consequence of making the sheets relatively bulky thereby making packaging more difficult. Additional fiber also increases the cost of the final wipe product. Pre-existing wipe products also tend to lack significant surface texture. Thus, scouring ability is relatively limited.

Diapers are well known for use in containing urine and bowel discharge. Modern diapers typically have a layered structure in which a user contact surface layer characterized by low moisture retention is disposed in overlying relation to a highly absorbent fiber layer which acts to lock expelled fluid in place. One or more intermediate wicking layers may be disposed between the user contact surface layer and the fluid absorption layer. In general, it is desirable to move fluid away from the user's skin as quickly as possible. However, there may be some delay in achieving full absorption of fluid into the absorbent layer. This may slow down the rate of fluid removal from the user's skin surface.

In light of the above, there is a continuing need for an improved wipe product which may act as a carrier for disinfecting solution and which has a scouring surface adapted to promote aggressive cleaning without failure. There is also a continuing need for an improved diaper construction which facilitates efficient removal of fluid from a user's skin surface.

SUMMARY OF THE DISCLOSURE

The present disclosure provides advantages and alternatives over the prior art by providing a stitch-bonded fabric construction in which broadly spaced parallel linear stitch lines are applied through a very low weight spun bonded substrate or the like to stabilize the substrate in the machine direction. Texture is imparted by applying significant overfeed conditions to the stitching substrate thereby causing a substantial bunching of the substrate at the stitching position. The resulting product has an arrangement of alternating ridges and valleys running predominantly in the cross-machine direction. The linear stitch lines define lateral sides of crater-like depressions between adjacent ridges. The stabilizing linear stitch lines lock in the puckered texture. The fabric construction may be saturated with a sanitizing or cleaning solution if desired. The substantially inelastic character of the linear stitch lines acts to lock in the textured construction.

In accordance with one exemplary aspect, the present disclosure provides a cleaning wipe of stitch-bonded construction. The wipe includes a stitching substrate of fibrous nonwoven material having a mass per unit area of not more than about 30 grams per square meter. A plurality of stitching yarns are disposed in stitched relation through the stitching substrate in a pattern of substantially parallel linear stitch lines extending in the machine direction across the stitching substrate. The linear stitch lines are spaced apart from one another by a significant distance. The stitching substrate is delivered to the stitching position at a substantial surplus such that it bunches and is consolidated during stitching. The stitching substrate is delivered to the stitch-forming position with at least 25% overfeed (i.e. surplus) relative to the rate of discharge from the take-up rolls such that one meter of stitching substrate yields no more than about 0.75 meters of stitched product. The surplus stitching substrate forms an arrangement of surface ridges running predominantly in the cross-machine direction with valleys disposed between the surface ridges. The stabilizing linear stitch lines lock in the texture-imparting ridges and valleys and define lateral sides of crater-like depressions between adjacent ridges. A disinfecting and/or cleaning solution may at least partially saturate the cleaning wipe.

In accordance with another exemplary aspect, the present disclosure provides a stitch-bonded fluid acquisition layer for a diaper disposed at an intermediate position between the user contact layer and the highly absorbent fluid retention layer. The fluid acquisition layer is highly permeable and includes a stitching substrate of fibrous nonwoven material having a mass per unit area of not more than about 30 grams per square meter. A plurality of stitching yarns are disposed in stitched relation through the stitching substrate in a pattern of substantially parallel linear stitch lines extending in the machine direction across the stitching substrate. The linear stitch lines are spaced apart from one another by a significant distance. The stitching substrate is delivered to the stitching position at a substantial surplus such that it bunches and is consolidated during stitching. The stitching substrate is delivered to the stitch-forming position with at least 25% overfeed (i.e. surplus) relative to the rate of discharge from the take-up rolls such that one meter of stitching substrate yields no more than about 0.75 meters of stitched product. The surplus stitching substrate forms an arrangement of surface ridges running predominantly in the cross-machine direction with valleys disposed between the surface ridges. The stabilizing linear stitch lines lock in the texture-imparting ridges and valleys and define lateral sides of crater-like depressions between adjacent ridges. The highly textured fluid acquisition layer collects and holds fluid in the crater-like depressions for dissipation into an underlying fluid absorption layer. This is believed to improve the efficiency of fluid removal from the user's skin surface.

BRIEF DESCRIPTION OF THE DRAWINGS

The accompanying drawings which are incorporated in and which constitute a part of this specification illustrate exemplary constructions and procedures in accordance with the present disclosure and, together with the general description of the disclosure given above and the detailed description set forth below, serve to explain the principles of the disclosure wherein:

FIG. 1 illustrates schematically a single bar stitch bonding system and take-up for forming a stitch-bonded fabric construction of creped character according to the present disclosure by stitching a pattern of parallel stabilizing stitch lines yarns running in the machine direction through a light-weight substrate material delivered at a substantial overfeed condition;

FIG. 2 illustrates one potential stitch pattern.

FIG. 3 is a scanned image of an exemplary creped material formed by the system of FIG. 1 illustrating stabilizing yarns running in parallel stitch lines along the machine direction retaining the substrate in a pattern of crater-like depressions bounded by cross-machine ridges and machine-direction stabilizing yarns; and FIG. 4 is a schematic cross-section of one exemplary layered diaper construction incorporating the stitch-bonded creped material of the present disclosure as a fluid acquisition layer.

Before the exemplary embodiments are explained in detail, it is to be understood that the invention is in no way limited in its application or construction to the details and the arrangements of the components set forth in the following description or illustrated in the drawings. Rather, the invention is capable of other embodiments and being practiced or being carried out in various ways. It is intended that the present disclosure shall extend to all alternatives and modifications as may embrace the general principles of the invention within the full and true spirit and scope thereof. Also, it is to be understood that the phraseology and terminology used herein are for purposes of description only and should not be regarded as limiting. The use herein of terms such as "including" and "comprising" and variations thereof is meant to encompass the items listed thereafter and equivalents thereof as well as additional items and equivalents thereof.

DESCRIPTION OF THE PREFERRED EMBODIMENTS

Reference will now be made to the drawings, wherein to the extent possible like reference numerals are used to designate like elements in the various views. In FIG. 1, a so called single bar stitch-bonding process is illustrated schematically. In the illustrated exemplary practice, one or more plies of a substrate material 30 of fibrous nonwoven construction such as a spunbonded fleece or the like is conveyed to a stitch-forming position in the direction indicated by the arrows. By way of example only, the substrate material 30 may be a spunbonded polyester or polypropylene fleece having a mass per unit area of about 5 to about 30 grams per square meter and more preferably about 12-16 grams per square meter. However, other materials with higher or lower weights may also be used. While FIG. 1 illustrates the use of a single ply of substrate material, it is also contemplated that multiple plies also may be used if desired.

As will be appreciated by those of skill in the art, during the stitch-bonding process a needle 34 (shown in greatly exaggerated dimension) pierces the substrate material 30 and engages stitching yarns 36 delivered into position by the yarn guide such that the stitching yarns are captured within a hook portion of the needle 34. By way of example only, and not limitation, the stitching yarns 36 may be multifilament polyester yarns or the like having a linear density in the range of about 20 to 150 denier, although heavier or lighter yarns may be used if desired. One potentially preferred yarn is a 40 denier, 12 filament fully oriented polyester, although other yarns may be used if desired. As the needle is reciprocated downwardly, a closing element such as a closing wire which moves relative to the needle 34 closes the hook portion to hold the stitching yarns therein. With the hook portion closed, the captured stitching yarns are pulled through the interior of an immediately preceding yarn loop disposed around the shank of the needle 34 at a position below the substrate material 30. As the captured stitching yarns are pulled through the interior of the preceding yarn loop a stitch is formed which is knocked off of the needle 34. As the needle 34 is raised back through the substrate material 30, the hook portion is reopened and a new yarn loop moves out of the hook portion and is held around the shank of the needle 34 for acceptance of captured yarns and formation of a subsequent stitch during the next down stroke. As this process is repeated multiple times at multiple needles 34, a resultant stitch-bonded fabric 38 is thus produced. In this regard, while only a single needle 34 is shown engaging a single stitching yarn 36, in actual practice, multiple needles 34 are disposed in spaced-apart, side by side relation across the width of the substrate material 30 to each engage a stitching yarn 36 in a manner as will be well understood to those of skill in the art.

In practice, the substrate material 30 may be held down on either side of each needle 34 by a low profile hold down sinker 40. According to one exemplary practice, in order to impart functional tear lines across the fabric, the stitch-bonded fabric 38 may be periodically subjected to localized melt fusion and/or perforation at a station 44 downstream from the needling position. As will be appreciated, the application of a melt fusion line and/or localized perforation line defines a stress concentrator to facilitate controlled tearing during use. That is, the material will have sufficient strength to permit rolling but application of a shear force along the perforation line will cause controlled tearing.

In accordance with the preferred practice, the substrate material is delivered to the needling position at a substantial overfeed condition of greater than about 25% and more preferably, about 40% or higher and most preferably about 50% or higher. In one potentially desirable construction illustrated in FIG. 2, the substrate material 30 is delivered at about 60% overfeed. In this regard, it is to be understood that the term "overfeed" refers to the percentage difference between a defined linear distance of substrate material 30 fed into the stitching position and the resultant linear distance of stitch-bonded fabric 38 collected by the take-up roll. This ratio may be adjusted by varying the rate of substrate delivery relative to the rate of stitched fabric take-up. By way of example, in the event that one meter of substrate material 30 is delivered to the stitching position and is consolidated to 0.4 meters of stitch-bonded fabric following take-up, the overfeed is 60%. Likewise, in the event that one meter of substrate material 30 is delivered to the stitching position and is consolidated to 0.7 meters of stitch-bonded fabric 38 following take-up, the overfeed is 30%.

As best seen in FIG. 3, the presence of excess substrate material 30 causes the substrate to bunch up and pucker at the needling position and to form a pattern of alternating raised ridges and depressed valleys of alluvial character oriented with major length dimensions predominantly in the cross-machine direction. Normally, bunching and puckering is considered a defect and is avoided if possible. As shown, the stitching yarns 36 are stitched into relatively widely spaced parallel linear stitch lines 50 which run in the machine direction (i.e. the direction of travel of the substrate material 30. These linear stitch lines 50 act to lock in the puckered character of the substrate material 30. In this regard, the linear stitch lines 50 act to compress the ridges at the location of contact and define lateral sides to crater-like depressions of substantial depth between adjacent ridges. In the stitch-bonded fabric 38, the crater-like depressions on one side cooperatively define the ridges on the opposite side.

As will be appreciated, each of the linear stitch lines 50 is formed by an individual reciprocating needle 34 (only one shown) with a row of such needles extending in adjacent relation to one another across the width of the substrate material 30 substantially transverse to the direction of movement of the substrate material 30. The so called gauge or needle density in the cross machine direction maybe adjusted as desired. By way of example only, and not limitation, it is contemplated that the gauge may be in the range of about 7 to 28 needles per inch and will more preferably be about 12 to 16 needles per inch and will most preferably be about 14 needles per inch. However, higher and lower needle densities may likewise be used if desired. By way of example only, and not limitation, it is contemplated that the stitch bonding machine may be set to apply about 10 to 16 stitches per inch and most preferably about 12 stitches per inch along each stitch line 50 in the machine direction (also known as courses per inch or CPI).

By way of example only, and not limitation, the stitch lines 50 may be formed by stitching the yarns 36 through the substrate material 30 in a pattern of parallel, spaced apart chain stitches extending along the machine direction in a partially threaded arrangement. By way of example, an exemplary stitch pattern notation for the linear stitch lines may be (1-0,0-1//). The distance between the linear stitch lines 50 is preferably at least about 3 mm and will more preferably be in the range of about 5 mm to about 12 mm although greater or lesser spacing distances may be used. In the illustrated exemplary construction of FIG. 2, the stitching yarns 36 are threaded in a so called "1 miss 4" pattern with every fifth needle being engaged. Of course, other partial threading arrangements such as "1 miss 2", "1 miss 3", "1 miss 5", "1 miss 6" etc. may be used if desired. It has been found that in at least some instances leaving the unthreaded intermediate needles in place may be beneficial in promoting processing in the desired overfeed condition. Perforation by these unthreaded needles continues to occur such that small needle holes are produced through the substrate material across the width of the stitch-bonded fabric 38 between the individual stitch lines 50. These needle holes are oriented in linear relation to one another and to the individual stitches in the stitch lines across the width of the stitch-bonded fabric 38.

The stitch-bonded material and resulting products according to the present disclosure are characterized by relatively limited stretch in the machine direction due to the presence of the linear stitch lines. In this regard, the stretch before failure in the machine direction is preferably less than 20% and is more preferably less than 10%. The absence of substantial machine direction stretch is believed to promote maintaining the presence of the texture-imparting ridges and valleys across the surface during use.

As noted previously, in one application, the stitch bonded constructions described may be used as a cleaning wipe. If desired, such cleaning wipes may be saturated with a disinfecting or cleaning solution by techniques such as spraying, immersion or the like as will be known to those of skill in the art and packaged as rolls with periodic tear lines to permit withdrawal and use for cleaning and disinfecting purposes. The presence of the ridges and valleys provides a textured scrubbing surface to facilitate the cleaning function.

In another application, the stitch-bonded fabric 38 such as illustrated in FIG. 2 may be used as a relatively light-weight fluid acquisition layer in a diaper disposed in overlying relation to a highly absorbent fluid retention layer. By way of example only, and not limitation, FIG. 4 illustrates one exemplary layered arrangement 70 for a diaper. The layered arrangement 70 includes a user contact layer 72 of highly permeable, non-absorptive character which is adapted to pass fluid while remaining relatively dry. An optional fibrous wicking layer 74 of generally hydrophobic character may be disposed below the user contact layer 72 to facilitate moving fluid away from the user. A fluid acquisition layer 76 formed by the stitch-bonded fabric 38 of creped construction as described may be disposed at an intermediate position below the user contact layer 72 and above a highly absorbent fluid retention layer 78. An optional, fluid barrier layer 80 may be disposed at a position behind the fluid retention layer 78. Of course, any number of additional layers may be introduced between any of the layers if desired.

In operation, the fluid acquisition layer is not highly absorptive but may act to hold a relatively large volume of fluid in a readily releasable manner for delivery to the underlying fluid retention layer 78. In particular, it is contemplated that the fluid will pool in the available craters across the surface of the fluid acquisition layer 76. It thus acts as a reservoir for collecting and holding fluid away from a user until it can be absorbed within the fluid retention layer 78.

Of course, variations and modifications of the foregoing are within the scope of the present disclosure. Thus, it is to be understood that the disclosure disclosed and defined herein extends to all alternative combinations of two or more of the individual features mentioned or evident from the text and/or drawings. All of these different combinations constitute various alternative aspects of the present disclosure. The embodiments described herein explain the best modes known for practicing the disclosure and will enable others skilled in the art to utilize the disclosure. The claims are to be construed to include alternative embodiments and equivalents to the extent permitted by the prior art.

What is claimed is:

1. A method of forming a stitch-bonded creped fabric, comprising the steps of: delivering a stitching substrate of fibrous nonwoven fleece to a stitching position in a stitch-bonding apparatus, the stitching substrate having a mass per unit area of not more than about 30 grams per square meter; and stitching a plurality of yarns in a pattern of substantially parallel spaced-apart linear stitch lines extending in the machine direction across the stitching substrate to form the stitch-bonded fabric, wherein the stitching substrate is delivered to the stitching position at a rate in excess of the rate of take-up from the stitching position such that the stitching substrate bunches and is consolidated during stitching, the stitching substrate being delivered to the stitching position with at least 25% overfeed relative to the rate of discharge such that delivery of one meter of stitching substrate in the machine direction yields no more than about 0.75 meters of stitch-bonded fabric in the machine direction, wherein the stitching substrate forms an arrangement of texture-imparting ridges running predominantly in the cross-machine direction of the stitch-bonded fabric and wherein the stitch-bonded fabric is characterized by stretch before failure in the machine direction of less than 20%.

2. The method as recited in claim 1, comprising the further step of applying a cleaning or disinfecting solution to the stitch-bonded fabric.

3. The method as recited in claim 1, wherein the stitching substrate is spunbonded polyester or polypropylene fleece.

4. The method as recited in claim 3, wherein the stitching substrate has a mass per unit area of about 5 grams per square meter to about 20 grams per square meter.

5. The method as recited in claim 1, wherein the stitching substrate being delivered to the stitching position with at least 40% overfeed relative to the rate of discharge such that one meter of stitching substrate yields no more than about 0.6 meters of stitch-bonded fabric.

6. The method as recited in claim 1, wherein the stitching substrate being delivered to the stitching position with at least 50% overfeed relative to the rate of discharge such that one meter of stitching substrate yields no more than about 0.5 meters of stitch-bonded fabric.

7. The method as recited in claim 1, wherein the stitching substrate being delivered to the stitching position with at least 60% overfeed relative to the rate of discharge such that one meter of stitching substrate yields no more than about 0.4 meters of stitch-bonded fabric.

8. The method as recited in claim 1, wherein the linear stitch lines are spaced apart by a distance of not less than about 3 mm.

9. The method as recited in claim 8, wherein a plurality of needle perforations devoid of stitching yarns are disposed between the linear stitch lines.

10. The method as recited in claim 8, wherein the linear stitch lines are spaced apart by a distance of not less than about 5 mm.

11. The method as recited in claim 10, wherein a plurality of needle perforations devoid of stitching yarns are disposed between the linear stitch lines.

12. The method as recited in claim 10, wherein the linear stitch lines are spaced apart by a distance of about 5 mm to about 12 mm.

13. The method as recited in claim 12, wherein a plurality of needle perforations devoid of stitching yarns are disposed between the linear stitch lines.

\* \* \* \* \*